(12) United States Patent
Hillier et al.

(10) Patent No.: US 12,077,616 B2
(45) Date of Patent: Sep. 3, 2024

(54) PRODUCTION OF POLYETHYLENE AND ETHYLENE OLIGOMERS FROM ETHANOL AND THE USE OF BIOMASS AND WASTE STREAMS AS FEEDSTOCKS TO PRODUCE THE ETHANOL

(71) Applicant: Chevron Phillips Chemical Company LP, The Woodlands, TX (US)

(72) Inventors: James Hillier, Kingwood, TX (US); Michael S. Webster-Gardiner, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 259 days.

(21) Appl. No.: 17/551,273

(22) Filed: Dec. 15, 2021

(65) Prior Publication Data
US 2023/0183390 A1    Jun. 15, 2023

(51) Int. Cl.
*C08F 2/34* (2006.01)
*C08F 4/78* (2006.01)

(52) U.S. Cl.
CPC ............ *C08F 2/34* (2013.01); *C08F 4/78* (2013.01); *Y02E 50/10* (2013.01); *Y02E 50/30* (2013.01); *Y02P 20/143* (2015.11); *Y02P 20/145* (2015.11)

(58) Field of Classification Search
CPC ... C08F 2/34; C08F 4/78; Y02E 50/30; Y02E 50/10; Y02P 20/145; Y02P 20/143
See application file for complete search history.

(56) References Cited

U.S. PATENT DOCUMENTS

| | | |
|---|---|---|
| 2,825,721 A | 3/1958 | Hogan |
| 3,225,023 A | 12/1965 | Hogan |
| 3,226,205 A | 12/1965 | Rohlfing |
| 3,242,099 A | 3/1966 | Manyik |
| 3,248,179 A | 4/1966 | Norwood |
| 3,622,521 A | 11/1971 | Hogan |

(Continued)

FOREIGN PATENT DOCUMENTS

| | | | | |
|---|---|---|---|---|
| EP | 3907209 A1 | * | 11/2021 | ............. C07C 1/20 |
| WO | 2020223335 A1 | | 11/2020 | |

OTHER PUBLICATIONS

International Search Report and Written Opinion issued in related application No. PCT/US2022/080757, mailed on Mar. 29, 2023, 10 pp.

(Continued)

*Primary Examiner* — Catherine S Branch
(74) *Attorney, Agent, or Firm* — Merchant & Gould P.C.

(57) ABSTRACT

Processes for producing ethylene-based polymers and oligomers from ethanol include the steps of contacting the ethanol and a catalyst to produce a reaction mixture containing ethylene, wherein a first portion of the ethanol is derived from a biomass and a second portion of the ethanol is derived from a plastic, a mixed solid waste stream, or a combination thereof, separating at least a portion of the ethylene from the reaction mixture, and contacting ethylene with a suitable polymerization or oligomerization catalyst composition to produce the ethylene polymer or ethylene oligomers. A related process for producing ethylene-based polymers and oligomers uses a first ethylene feed derived from ethanol and a second ethylene feed derived from a plastic, a mixed solid waste stream, or a combination thereof.

20 Claims, 8 Drawing Sheets

(56) References Cited

U.S. PATENT DOCUMENTS

| | | |
|---|---|---|
| 3,625,864 A | 12/1971 | Horvath |
| 3,887,494 A | 6/1975 | Dietz |
| 3,900,457 A | 8/1975 | Witt |
| 3,976,632 A | 8/1976 | Delap |
| 4,053,436 A | 10/1977 | Hogan |
| 4,081,407 A | 3/1978 | Short |
| 4,151,122 A | 4/1979 | Mcdaniel |
| 4,182,815 A | 1/1980 | Mcdaniel |
| 4,247,421 A | 1/1981 | Mcdaniel |
| 4,248,735 A | 2/1981 | Mcdaniel |
| 4,296,001 A | 10/1981 | Hawley |
| 4,297,460 A | 10/1981 | Mcdaniel |
| 4,301,034 A | 11/1981 | Mcdaniel |
| 4,339,559 A | 7/1982 | Mcdaniel |
| 4,364,842 A | 12/1982 | Mcdaniel |
| 4,364,854 A | 12/1982 | Mcdaniel |
| 4,364,855 A | 12/1982 | Mcdaniel |
| 4,392,990 A | 7/1983 | Witt |
| 4,397,766 A | 8/1983 | Hawley |
| 4,397,769 A | 8/1983 | Mcdaniel |
| 4,405,501 A | 9/1983 | Witt |
| 4,444,962 A | 4/1984 | Mcdaniel |
| 4,444,964 A | 4/1984 | Mcdaniel |
| 4,444,965 A | 4/1984 | Mcdaniels |
| 4,460,756 A | 7/1984 | Mcdaniel |
| 4,501,885 A | 2/1985 | Sherk |
| 4,504,638 A | 3/1985 | Mcdaniel |
| 4,547,557 A | 10/1985 | Mcdaniel |
| 4,588,790 A | 5/1986 | Jenkins, III |
| 4,735,931 A | 4/1988 | Mcdaniel |
| 4,806,513 A | 2/1989 | Mcdaniel |
| 4,808,561 A | 2/1989 | Welborn, Jr. |
| 4,820,785 A | 4/1989 | Mcdaniel |
| 4,855,271 A | 8/1989 | Mcdaniel |
| 4,939,217 A | 7/1990 | Stricklen |
| 4,981,831 A | 1/1991 | Knudsen |
| 4,988,657 A | 1/1991 | Martin |
| 5,037,911 A | 8/1991 | Mcdaniel |
| 5,179,178 A | 1/1993 | Stacy |
| 5,191,132 A | 3/1993 | Patsidis |
| 5,210,352 A | 5/1993 | Alt |
| 5,219,817 A | 6/1993 | Mcdaniel |
| 5,221,654 A | 6/1993 | Mcdaniel |
| 5,237,025 A | 8/1993 | Benham |
| 5,244,990 A | 9/1993 | Mitchell |
| 5,275,992 A | 1/1994 | Mitchell |
| 5,347,026 A | 9/1994 | Patsidis |
| 5,352,749 A | 10/1994 | Dechellis |
| 5,399,636 A | 3/1995 | Alt |
| 5,401,817 A | 3/1995 | Palackal |
| 5,420,320 A | 5/1995 | Zenk |
| 5,436,304 A | 7/1995 | Griffin |
| 5,436,305 A | 7/1995 | Alt |
| 5,451,649 A | 9/1995 | Zenk |
| 5,480,848 A | 1/1996 | Geerts |
| 5,496,781 A | 3/1996 | Geerts |
| 5,498,581 A | 3/1996 | Welch |
| 5,541,272 A | 7/1996 | Schmid |
| 5,554,795 A | 9/1996 | Frey |
| 5,563,284 A | 10/1996 | Frey |
| 5,565,175 A | 10/1996 | Hottovy |
| 5,565,592 A | 10/1996 | Patsidis |
| 5,571,880 A | 11/1996 | Alt |
| 5,575,979 A | 11/1996 | Hanson |
| 5,594,078 A | 1/1997 | Welch |
| 5,610,247 A | 3/1997 | Alt |
| 5,627,247 A | 5/1997 | Alt |
| 5,631,203 A | 5/1997 | Welch |
| 5,631,335 A | 5/1997 | Alt |
| 5,654,454 A | 8/1997 | Peifer |
| 5,668,230 A | 9/1997 | Schertl |
| 5,705,579 A | 1/1998 | Hawley |
| 6,239,235 B1 | 5/2001 | Hottovy |
| 6,262,191 B1 | 7/2001 | Hottovy |
| 6,300,271 B1 | 10/2001 | Mcdaniel |
| 6,355,594 B1 | 3/2002 | Mcdaniel |
| 6,395,666 B1 | 5/2002 | Mcdaniel |
| 6,548,442 B1 | 4/2003 | Mcdaniel |
| 6,613,712 B1 | 9/2003 | Mcdaniel |
| 6,653,416 B2 | 11/2003 | Mcdaniel |
| 6,831,141 B2 | 12/2004 | Mcdaniel |
| 6,833,338 B2 | 12/2004 | Mcdaniel |
| 6,833,415 B2 | 12/2004 | Kendrick |
| 7,026,494 B1 | 4/2006 | Yang |
| 7,041,617 B2 | 5/2006 | Jensen |
| 7,199,073 B2 | 4/2007 | Martin |
| 7,226,886 B2 | 6/2007 | Jayaratne |
| 7,294,599 B2 | 11/2007 | Jensen |
| 7,312,283 B2 | 12/2007 | Martin |
| 7,417,097 B2 | 8/2008 | Yu |
| 7,517,939 B2 | 4/2009 | Yang |
| 7,531,606 B2 | 5/2009 | Hendrickson |
| 7,598,327 B2 | 10/2009 | Shaw |
| 7,619,047 B2 | 11/2009 | Yang |
| 7,863,489 B2 | 1/2011 | Johnston |
| 7,919,639 B2 | 4/2011 | Murray |
| 8,080,681 B2 | 12/2011 | Murray |
| 8,440,873 B2 | 5/2013 | Bailey |
| 8,822,608 B1 | 9/2014 | Bhandarkar |
| 9,422,494 B2 | 8/2016 | Bradin |
| 10,435,336 B2 | 10/2019 | Kreischer |
| 10,464,862 B2 | 11/2019 | Bischof |
| 10,493,422 B2 | 12/2019 | Bischof |
| 10,689,312 B2 | 6/2020 | Bischof |
| 10,807,921 B2 | 10/2020 | Kilgore |
| 11,124,708 B2 | 9/2021 | Vermeiren |
| 2013/0143973 A1 | 6/2013 | Townsend |
| 2016/0375431 A1 | 12/2016 | Carney |
| 2017/0081257 A1 | 3/2017 | Kreischer |
| 2017/0341998 A1 | 11/2017 | Bischof |
| 2017/0341999 A1 | 11/2017 | Fern |
| 2017/0342000 A1 | 11/2017 | Bischof |
| 2017/0342001 A1 | 11/2017 | Fern |
| 2021/0207038 A1 | 7/2021 | Vermeiren |

OTHER PUBLICATIONS

Kang, J., He, S., Zhou, W. et al. Single-pass transformation of syngas into ethanol with high selectivity by triple tandem catalysis. Nat Commun 11, 827 (2020). https://doi.org/10.1038/s41467-020-14672-8.

* cited by examiner

PRODUCTION OF POLYETHYLENE AND ETHYLENE OLIGOMERS FROM ETHANOL AND THE USE OF BIOMASS AND WASTE STREAMS AS FEEDSTOCKS TO PRODUCE THE ETHANOL

FIELD OF THE INVENTION

The present disclosure generally relates to methods for making ethylene polymers and ethylene oligomers from ethylene, and more particularly, relates to performing such methods using ethylene derived from biomass or a plastic or solid waste stream either directly or from ethanol.

BACKGROUND OF THE INVENTION

Plastic waste and its environmental impact are an ongoing problem. Current efforts to recycle waste plastics include pyrolysis, which can generate liquid feedstocks, and gasification of waste plastics to generate a Syngas (largely, a mixture of carbon monoxide and hydrogen gas).

Ethylene is an important feedstock for the production of ethylene-based polymers, such as polyethylene, and ethylene-based oligomers, such as 1-hexene and 1-octene. Ethylene can be produced from ethanol, which can be bio-based and produced by plants consuming $CO_2$ from the atmosphere.

It would be beneficial to use a combination of these technologies to produce bio-based ethylene polymers and oligomers. Accordingly, it is to this end that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Aspects of this invention are directed to processes for producing ethylene-based polymers and oligomers. In accordance with one aspect of this invention, a first process for converting ethanol into an ethylene polymer and/or ethylene oligomers can comprise (a) contacting the ethanol and a catalyst to produce a reaction mixture containing ethylene, wherein a first portion of the ethanol is derived from a biomass and a second portion of the ethanol is derived from a plastic, a mixed solid waste stream, or a combination thereof, (b) separating at least a portion of the ethylene from the reaction mixture, and (c1) contacting a polymerization catalyst composition with the ethylene and an optional olefin comonomer in a polymerization reactor system under polymerization conditions to produce the ethylene polymer, and/or (c2) contacting an oligomerization catalyst composition with the ethylene in an oligomerization reactor system under oligomerization conditions to produce the ethylene oligomers.

In accordance with another aspect of this invention, a second process for producing an ethylene polymer and/or ethylene oligomers can comprise (A) contacting ethanol and a catalyst to produce a reaction mixture containing ethylene, wherein a first portion of the ethanol is derived from a biomass and an optional second portion of the ethanol is derived from a plastic, a mixed solid waste stream, or a combination thereof, (B) separating at least a portion of the ethylene from the reaction mixture to form a first ethylene feed, and (C1) contacting a polymerization catalyst composition, a feed mixture of the first ethylene feed and a second ethylene feed, and an optional olefin comonomer in a polymerization reactor system under polymerization conditions to produce the ethylene polymer, and/or (C2) contacting an oligomerization catalyst composition with a feed mixture of the first ethylene feed and a second ethylene feed in an oligomerization reactor system under oligomerization conditions to produce the ethylene oligomers. The second ethylene feed is derived from a plastic, a mixed solid waste stream, or a combination thereof.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

Figure 1:
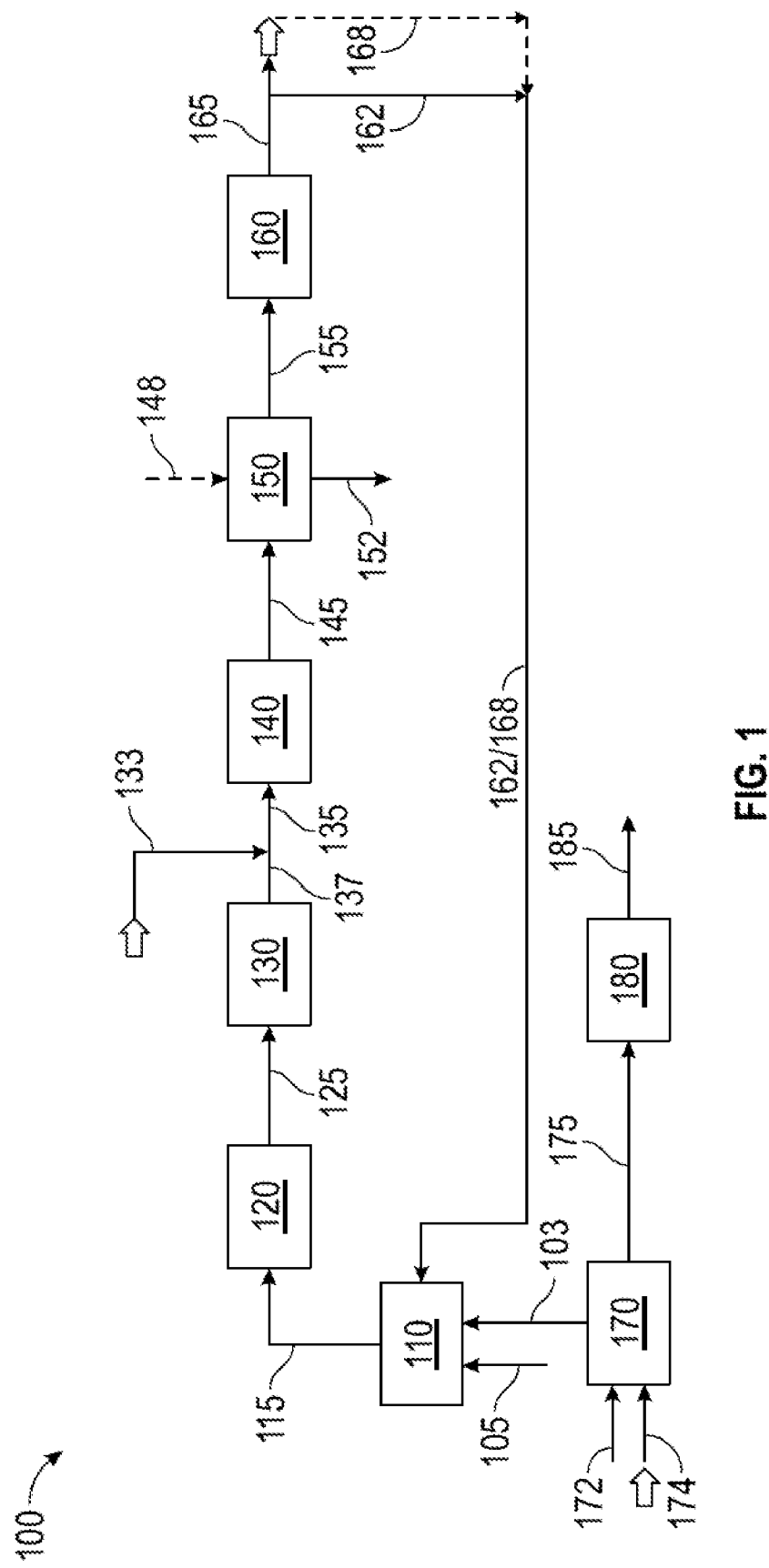
FIG. 1 is a schematic flow diagram of a process for converting ethanol into an ethylene polymer and/or ethylene oligomers consistent with an aspect of the present disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the processes or methods described herein are contemplated with or without explicit description of the particular combination. Additionally, unless explicitly recited otherwise, any aspect or feature disclosed herein can be combined to describe inventive processes or methods consistent with the present disclosure.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). Non-limiting examples of hydrocarbons include alkanes (linear, branched, and cyclic), alkenes (olefins), and aromatics, among other compounds.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contacting" and "combining" are used herein to describe catalysts, compositions, processes, and methods in which the materials or components are contacted or combined together in any order, in any manner, and for any length of time, unless otherwise specified. For example, the materials or components can be blended, mixed, slurried, dissolved, reacted, treated, impregnated, compounded, or otherwise contacted or combined in some other manner or by any suitable method or technique.

In this disclosure, while processes and methods are described in terms of "comprising" various components or steps, the processes and methods also can "consist essentially of" or "consist of" the various components or steps, unless stated otherwise. The terms "a," "an," and "the" are intended to include plural alternatives, e.g., at least one, unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, ethanol used in the processes can be from two sources in any suitable relative proportions. By a disclosure that a weight ratio of the first portion of the ethanol (derived from a biomass) to the second portion of the ethanol (derived from a plastic, a mixed solid waste stream, or a combination thereof) can be in a range from 50:1 to 1:50, the intent is to recite that the weight ratio can be any amount in the range and, for example, can include any range or combination of ranges from 50:1 to 1:50, such as from 10:1 to 1:10, from 5:1 to 1:5, or from 2:1 to 1:2, and so forth. Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods, devices, and materials similar or equivalent to those described herein can be used in the practice or testing of the invention, the typical methods, devices, and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

The present invention is generally directed to combining existing technologies to replace fossil-based feedstock ethylene with bio-based ethylene for the production of polyethylene and simultaneously generate a pathway for circular polyethylene. In one aspect, this can be accomplished by using ethanol as a key common intermediate material to produce ethylene, and subsequently polyethylene.

A key objective of the present invention is to combine known processes with emerging research to generate a pathway to produce a bio-based polyethylene, which also has as part of the pathway a means for recycling to generate a polyethylene that has the same composition and properties as that generated from conventional means, but in which fossil-based ethylene is not the sole feedstock for polyethylene production.

Another key objective is to use renewable feedstocks and circular feedstocks to produce ethanol, then convert to ethylene, and subsequently polyethylene. The ethanol can be derived from a number of different sources.

Another key objective is to combine the production of ethanol from a bio-based source and the production of ethanol from recycled plastic, biomass, or municipal solid waste, or combinations of these sources. For instance, this latter ethanol can result from gasification of the suitable source material to produce Syngas, which can then be catalytically converted to form ethanol. Ethanol, and therefore ethylene, can be derived from a bio-based source and/or derived from a waste/recycle-based source.

Another key objective is to vary the amount of circular ethanol/ethylene feedstocks used in the process, such that depending upon market and environmental forces, for instance, the feedstocks can range from 99% bio-based to 99% non-bio-based and/or from 99% circular to 99% non-circular, and any combination in between. Accordingly, a portion of the ethanol/ethylene feedstocks can be derived from fossil fuel sources, if desired.

Another key objective is to utilize water electrolysis and cryogenic air separation to generate $H_2$, $O_2$, and $N_2$, and to utilize the $O_2$ for gasification and to utilize the $H_2$ and $N_2$ to produce ammonia. Further, $CO_2$ generated in the various processes disclosed herein can be reacted with ammonia to produce urea, which is an important fertilizer feedstock.

Processes for Producing Ethylene Polymers and Oligomers

Disclosed herein are processes for producing an ethylene-based polymer and/or ethylene-based oligomers. In one aspect consistent with this invention, a first process for converting ethanol into an ethylene polymer and/or ethylene oligomers can comprise (a) contacting the ethanol and a catalyst to produce a reaction mixture containing ethylene, wherein a first portion of the ethanol is derived from a biomass and a second portion of the ethanol is derived from a plastic, a mixed solid waste stream, or a combination thereof, (b) separating at least a portion (and in some cases, all) of the ethylene from the reaction mixture, and (c1) contacting a polymerization catalyst composition with the ethylene and an optional olefin comonomer in a polymerization reactor system under polymerization conditions to produce the ethylene polymer, and/or (c2) contacting an oligomerization catalyst composition with the ethylene in an oligomerization reactor system under oligomerization conditions to produce the ethylene oligomers. In the first process, the ethanol is derived from two sources.

In another aspect consistent with this invention, a second process for producing an ethylene polymer and/or ethylene oligomers can comprise (A) contacting ethanol and a catalyst to produce a reaction mixture containing ethylene, wherein a first portion of the ethanol is derived from a biomass and an optional second portion of the ethanol is derived from a plastic, a mixed solid waste stream, or a combination thereof, (B) separating at least a portion (and in some cases, all) of the ethylene from the reaction mixture to form a first ethylene feed, and (C1) contacting a polymerization catalyst composition, a feed mixture of the first ethylene feed and a second ethylene feed, and an optional olefin comonomer in a polymerization reactor system under polymerization conditions to produce the ethylene polymer, and/or (C2) contacting an oligomerization catalyst composition with a feed mixture of the first ethylene feed and a second ethylene feed in an oligomerization reactor system under oligomerization conditions to produce the ethylene oligomers. The second ethylene feed is derived from a plastic, a mixed solid waste stream, or a combination thereof. Thus, in the second process, the ethylene is derived from two sources, and the ethanol is derived from either one or two sources. While not limited thereto, in the second process, the weight ratio of the first ethylene feed to the second ethylene feed in the feed mixture can range from 50:1 to 1:50, but more often, this weight ratio of the first ethylene feed to the second ethylene feed falls within a range from 10:1 to 1:10, from 5:1 to 1:5, or from 2:1 to 1:2.

Generally, the features of the first and second processes (e.g., the sources of ethanol and ethylene, the conversion of ethanol to ethylene, the ethylene polymerization, and the ethylene oligomerization, among others) are independently described herein and these features can be combined in any combination to further describe the disclosed processes to produce ethylene polymers and/or ethylene oligomers. Moreover, additional process steps can be performed before, during, and/or after any of the steps in any of the processes disclosed herein and can be utilized without limitation and in any combination to further describe these processes, unless stated otherwise. Further, any ethylene polymers and/or ethylene oligomers produced in accordance with the disclosed processes are within the scope of this disclosure and are encompassed herein.

In a further aspect of the first process, a portion of the ethylene used in step (c1) and/or step (c2) can be ethylene derived from a fossil fuel source (e.g., crude oil, natural gas), and at any suitable relative amount, such as from 50:1 to 1:50, from 10:1 to 1:10, from 5:1 to 1:5, or from 2:1 to 1:2, and the like. The relative amount can vary depending upon market and environmental forces, for instance. Likewise, in a further aspect of the second process, in addition to the feed mixture, a third ethylene feed can be used in step (C1) and/or step (C2) and can be ethylene derived from a fossil fuel source, and similarly, at any suitable relative amount, such as from 50:1 to 1:50, from 10:1 to 1:10, from 5:1 to 1:5, or from 2:1 to 1:2, and the like.

Referring now to the first process, the weight ratio of the first portion of the ethanol to the second portion of the ethanol in step (a) is not particular limited, but generally ranges from 50:1 to 1:50, such as from 10:1 to 1:10, from 5:1 to 1:5, or from 2:1 to 1:2, and the like. In step (A) of the second process, when a second portion of the ethanol is used, the weight ratio of the first portion of the ethanol to the second portion of the ethanol in the second process also can fall within the same ranges, e.g., from 50:1 to 1:50, from 10:1 to 1:10, from 5:1 to 1:5, or from 2:1 to 1:2.

In step (a) of the first process and step (A) of the second process, ethanol is contacted with a catalyst to produce a reaction mixture containing ethylene. This step can be conducted in a vapor phase dehydration reactor. Suitable catalysts and reaction conditions for performing step (a) of the first process and step (A) of the second process are disclosed in U.S. Pat. No. 8,440,873.

For both the first and second processes, the first portion of the ethanol is derived from a biomass source. In an aspect, this first portion of the ethanol can be derived by fermenting the biomass to produce ethanol and a biomass by-product. In another aspect, this first portion of the ethanol can be derived by anaerobic digestion of the biomass source to produce ethanol and a biomass by-product. Optionally, the first and second process can further comprise a step of separating at least a portion (and in some cases, all) of the ethanol from the biomass by-product. Any suitable technique can be used for this separating step, non-limiting examples of which include extraction, filtration, evaporation, distillation, and the like, as well as any combination thereof.

The biomass is not particularly limited and can be any sugar source, grain source, cellulosic source, lignocellulosic source, and the like, as well as combinations thereof, that is suitable for fermentation (or anaerobic digestion) to produce ethanol. Corn, sugar beets, and sugar cane are illustrative examples of biomass sources that are often converted to bio-ethanol. Cellulosic and lignocellulosic biomass sources include waste timber, wood chips, sawdust, and the like, as well as combinations thereof.

Consistent with one aspect of this invention, the biomass source that can be used to produce ethanol (bio-ethanol) can be a first generation biomass source, and the first generation biomass source can include seed oils, sugars, and starch crops such as corn/maize, sugar cane, and the like, as well as combinations of two or more sources. In another aspect, the biomass source that can used to produce ethanol can be a second generation biomass source, and the second generation biomass source can include agricultural and forestry residues; dedicated energy crops like hybrid poplar, hemp, carrizo cane, and switchgrass; algae and genetically-modified versions of algae (e.g., nannochloropsis gaditana and variants thereof); municipal solid waste produced from cellulosic and lipid-rich plant materials that are not food crops; and including combinations of two or more of these sources. In yet another aspect, a combination of a first generation and a second generation source can be used as the biomass source, and at any suitable relative amounts. A potential advantage to the use of the second generation biomass source is that its use to produce a bio-ethanol or bio-fuel does not divert the biomass source from traditional food production (e.g., food versus fuel), as can be the case for the first generation biomass source.

Additionally or alternatively, this first portion of the ethanol can be derived by (i) gasifying a mixture of an oxygen-containing gasifying agent and the biomass (and/or the biomass by-product) to form a Syngas stream, (ii) separating CO and $H_2$ from the Syngas stream, and (iii) contacting the CO, $H_2$, and a multicomponent catalyst to form a reaction mixture containing ethanol.

The biomass source used for gasifying includes any of the sources used for fermentation provided hereinabove and the biomass source for gasifying may be the same as or different from the biomass source that is used for fermentation to produce ethanol. In an aspect, the biomass source used for fermentation comprises corn and/or sugar cane, while the biomass source for gasification includes a cellulosic and/or lignocellulosic material, a biomass by-product, or any combination thereof. Thus, biomass by-products from the biomass-to-ethanol fermentation process can be a biomass source for gasifying, one example of which is corn stover. And, as indicated above, the biomass source used for gasifying can be any suitable first generation biomass source, or any suitable second generation biomass source, or any combination thereof at any suitable relative amounts.

An illustrative and non-limiting example of the multicomponent catalyst that can be used in step (iii) can include a potassium-modified ZnO—$ZrO_2$, modified zeolite mordenite, and Pt—Sn/SiC. Other suitable catalysts and typical reaction conditions for step (iii) are disclosed in Kang et al., "Single-pass transformation of syngas into ethanol with high selectivity by triple tandem catalysts," Nature Communications, 2020, 11:827.

The second portion of the ethanol in the first process (and the optional second portion of the ethanol in the second process) is derived from a plastic, a mixed solid waste stream, or a combination thereof. In an aspect, this second portion of the ethanol can be derived by (i) gasifying a mixture of an oxygen-containing gasifying agent and the plastic, the mixed solid waste stream, or the combination thereof, to form a Syngas stream, (ii) separating CO and $H_2$ from the Syngas stream, and (iii) contacting the CO, $H_2$, and a multicomponent catalyst to form a reaction mixture containing ethanol. The mixed solid waste stream can be any suitable municipal waste source or sources, and the plastic can be virgin plastic or recycled plastic (e.g., post-consumer recycled plastic), as well as any combination thereof.

If gasification is used to produce the ethanol utilized in the first and second processes, the oxygen-containing gasifying agent can comprise $H_2O$ (steam), $O_2$, and/or $CO_2$. Typically, the nitrogen content of the gasifying agent is minimized, with the gasifying agent containing less than 1 mol % nitrogen in some aspects, and less than 0.5 mol % or less than 0.1 mol nitrogen in other aspects. Accordingly, air is not used as the gasifying agent in particular aspects of this invention. General information on gasification of biomass and other carbon-containing materials is disclosed in U.S. Patent Publication No. 2013/0143973. After gasifying in step (i) to form the Syngas stream, CO and $H_2$ can be separated in step (ii) from other components of the Syngas stream, such as $CO_2$, $N_2$, and $H_2O$, among others, using any suitable technique(s).

Also, when gasification is used, the first and second processes can further comprise a step of separating at least a portion (and in some cases, all) of the ethanol from the reaction mixture in step (iii) and prior to step (a) and step (A). This provides a higher purity ethanol feed for use in the first and second processes, and such can be accomplished using any suitable separating technique or combination of techniques, for instance, e.g., extraction, filtration, evaporation, distillation, and the like, as well as combinations thereof.

In step (b) of the first process, at least a portion (and in some cases, all) of the ethylene is separated from the reaction mixture, and in step (B) of the second process, at least a portion (and in some cases, all) of the ethylene is separated from the reaction mixture to form a first ethylene feed. This separating step provides a higher purity ethylene feed for use in the subsequent polymerization/oligomerization process steps. The separating in step (b) and step (B) can include any suitable technique or any technique disclosed herein, such as extraction, filtration, evaporation, distillation, and the like, as well as combination of two or more techniques.

The reaction mixture in step (a) and step (A) also can contain water, and optionally, the first and second processes can further comprise a step of separating or removing the water (all or any portion of) from the reaction mixture. As above, any suitable technique can be used in this separating step.

The step (c) options in the first process are (c1) contacting a polymerization catalyst composition with the ethylene and an optional olefin comonomer in a polymerization reactor system under polymerization conditions to produce the ethylene polymer, and/or (c2) contacting an oligomerization catalyst composition with the ethylene in an oligomerization reactor system under oligomerization conditions to produce the ethylene oligomers. Referring first to (c1), a polymerization catalyst composition is contacted with the ethylene and an optional olefin comonomer in a polymerization reactor system under polymerization conditions to produce the ethylene polymer. Polymerization catalyst compositions, comonomer options, polymerization reactor systems and suitable reactor types, polymerization conditions, and resulting ethylene polymers are well known to those of skill in the art.

Briefly, polymerization catalyst compositions that are suitable for use in the first and second process described herein include, but are not limited to, Ziegler-Natta based catalyst systems, chromium-based catalyst systems, metallocene-based catalyst systems, and the like, including combinations thereof. Hence, the polymerization catalyst composition can be a Ziegler-Natta based catalyst system, a chromium-based catalyst system, and/or a metallocene-based catalyst system; alternatively, a Ziegler-Natta based catalyst system; alternatively, a chromium-based catalyst system; or alternatively, a metallocene-based catalyst system. In one aspect, the polymerization catalyst composition can be a dual catalyst system comprising at least one metallocene compound, while in another aspect, the catalyst composition can be a dual catalyst system comprising two different metallocene compounds.

Examples of representative and non-limiting polymerization catalyst compositions include those disclosed in U.S. Pat. Nos. 3,887,494, 4,053,436, 4,981,831, 4,364,842, 4,444,965, 4,364,855, 4,504,638, 4,364,854, 4,444,964, 4,444,962, 3,976,632, 4,248,735, 4,297,460, 4,397,766, 2,825,721, 3,225,023, 3,226,205, 3,622,521, 3,625,864, 3,900,457, 4,301,034, 4,547,557, 4,339,559, 4,806,513, 5,037,911, 5,219,817, 5,221,654, 4,081,407, 4,296,001, 4,392,990, 4,405,501, 4,151,122, 4,247,421, 4,397,769, 4,460,756, 4,182,815, 4,735,931, 4,820,785, 4,988,657, 5,436,305, 5,610,247, 5,627,247, 3,242,099, 4,808,561, 5,275,992, 5,237,025, 5,244,990, 5,179,178, 4,855,271, 4,939,217, 5,210,352, 5,401,817, 5,631,335, 5,571,880, 5,191,132, 5,480,848, 5,399,636, 5,565,592, 5,347,026, 5,594,078, 5,498,581, 5,496,781, 5,563,284, 5,554,795, 5,420,320, 5,451,649, 5,541,272, 5,631,203, 5,654,454, 5,705,579, 5,668,230, 6,300,271, 6,831,141, 6,653,416, 6,613,712, 7,294,599, 6,355,594, 6,395,666, 6,833,338, 7,417,097, 6,548,442, 7,312,283, 7,026,494, 7,041,617, 7,199,073, 7,226,886, 7,517,939, 7,619,047, 7,919,639, and 8,080,681.

Such polymerization catalyst compositions, in addition to a transition metal, can contain an activator and an optional co-catalyst, and the catalyst system can be unsupported or supported on any suitable solid support (e.g., a porous solid oxide). Illustrative activators can include, but are not limited to, aluminoxane compounds (e.g., methylaluminoxane, MAO), organoboron or organoborate compounds, ionizing ionic compounds, activator-supports (e.g., a solid oxide treated with an electron-withdrawing anion), and the like, or combinations thereof. Commonly used polymerization co-catalysts can include, but are not limited to, organoaluminum and organozinc compounds, illustrative examples of which include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, dimethylzinc, diethylzinc (DEZ), dipropylzinc, dibutylzinc, dineopentylzinc, di(trimethylsilyl)zinc, di(triethylsilyl)zinc, di(triisoproplysilyl)zinc, di(triphenylsilyl)zinc, di(allyldimethylsilyl)zinc, di(trimethylsilylmethyl)zinc, and the like, or combinations thereof.

Suitable olefin comonomers that can be polymerized (e.g., copolymerized, terpolymerized) with ethylene can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to one aspect, the olefin comonomer can comprise an α-olefin (e.g., a $C_3$-$C_{10}$ α-olefin), while in another aspect, the comonomer can comprise propylene, 1-butene, 1-pentene, 1-hexene, 1-octene, or any combination thereof; alternatively, the olefin comonomer can comprise 1-butene, 1-hexene, 1-octene, or a combination thereof; alternatively, the olefin comonomer can comprise 1-butene; alternatively, the olefin comonomer can comprise 1-hexene; or alternatively, the olefin comonomer can comprise 1-octene.

The polymerization reactor system can include any polymerization reactor capable of polymerizing ethylene and an olefin comonomer(s) (if used) to produce ethylene-based homopolymers, copolymers, terpolymers, and the like. The various types of polymerization reactors include those that can be referred to as a batch reactor, slurry reactor, gas-phase reactor, solution reactor, high pressure reactor, tubular reactor, autoclave reactor, and the like, or combinations thereof; or alternatively, the polymerization reactor system can comprise a slurry reactor (e.g., a loop slurry reactor), a gas-phase reactor (e.g., a fluidized bed reactor), a solution reactor, or a combination thereof. The polymerization reactor system can comprise a single reactor or multiple reactors (2 reactors, more than 2 reactors) of the same or different type. For instance, the polymerization reactor system can comprise a slurry reactor, a gas-phase reactor, a solution reactor, or a combination of two or more of these reactors. Representative slurry polymerization reactors and/or processes are disclosed, for example, in U.S. Pat. Nos. 3,248,179, 4,501,885, 5,565,175, 5,575,979, 6,239,235, 6,262,191, 6,833,415, and 8,822,608, and representative gas phase or fluidized bed reactors and/or processes are disclosed in U.S. Pat. Nos. 5,352,749, 4,588,790, 5,436,304, 7,531,606, and 7,598,327.

The polymerization conditions for the various reactor types are well known to those of skill in the art. Nonetheless, a suitable polymerization temperature can be any temperature below the de-polymerization temperature according to the Gibbs Free energy equation. Typically, this includes from 60° C. to 280° C., for example, or from 60° C. to 120° C., depending upon the type of polymerization reactor(s). In some reactor systems, the polymerization temperature generally can be within a range from 70° C. to 105° C., or from 75° C. to 100° C. Suitable pressures will also vary according to the reactor and polymerization type. The pressure for liquid phase polymerizations in a loop reactor is typically less than 1000 psig (6.9 MPa). Pressure for gas phase polymerization is usually from 200 to 500 psig (1.4 MPa to 3.4 MPa). High pressure polymerization in tubular or autoclave reactors is generally run at from 20,000 psig to 75,000 psig (138 MPa to 517 MPa). Polymerization reactors can also be operated in a supercritical region occurring at generally higher temperatures and pressures. Operation above the critical point of a pressure-temperature diagram (supercritical phase) can offer advantages to the polymerization reaction process.

Generally, the ethylene polymer produced in the first and second processes can comprise an ethylene homopolymer and/or an ethylene/α-olefin copolymer in one aspect, and can comprise an ethylene homopolymer, an ethylene/1-butene copolymer, an ethylene/1-hexene copolymer, and/or an ethylene/1-octene copolymer in another aspect, and can comprise an ethylene/α-olefin copolymer and/or an ethylene terpolymer (e.g., ethylene with 1-butene and 1-hexene) in yet another aspect, and can comprise an ethylene/1-hexene copolymer in still another aspect.

Articles of manufacture can be formed from, and/or can comprise, the ethylene polymers of this invention and, accordingly, are encompassed herein. For example, articles which can comprise the polymers of this invention can include, but are not limited to, an agricultural film, an automobile part, a bottle, a container for chemicals, a drum, a fiber or fabric, a food packaging film or container, a food service article, a fuel tank, a geomembrane, a household container, a liner, a molded product, a medical device or material, an outdoor storage product (e.g., panels for walls of an outdoor shed), outdoor play equipment (e.g., kayaks, bases for basketball goals), a pipe, a sheet or tape, a toy, or a traffic barrier, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers often are added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992.

In some aspects of this invention, the article of manufacture can comprise any of ethylene polymers described herein, and the article of manufacture can be or can comprise a film, such as a blown film; alternatively, a pipe product; or alternatively, a blow molded product, such as a blow molded bottle.

Referring now to step (c2) of the first process, an oligomerization catalyst composition is contacted with the ethylene in an oligomerization reactor system under oligomerization conditions to produce the ethylene oligomers. Oligomerization catalyst compositions, oligomerization reactor systems and suitable reactor types, oligomerization conditions, and resulting ethylene oligomer products are well known to those of skill in the art. Briefly, an "oligomerization" process using ethylene as the monomer produces a mixture of products comprising at least 30 wt. %, 50 wt. %, 60 wt. %, or 70 wt. % oligomers having from 4 to 40 carbon atoms, or from 4 to 20 carbon atoms, such as a total amount of $C_6$ olefins and $C_8$ olefins of least 50 wt. %, 65 wt. %, 75 wt. %, or 80 wt. %.

Although not limited thereto, the oligomerization catalyst composition can be a chromium-based catalyst system. A particular example of an oligomerization catalyst composition can include a heteroatomic ligand chromium compound complex and an organoaluminum compound, or a heteroatomic ligand, a chromium compound, and an organoaluminum compound. Examples of representative and non-limiting oligomerization catalyst compositions—and ethylene oligomerization processes and reactor systems—include those disclosed in U.S. Patent Publication Nos. 2017/0081257, 2017/0341998, 2017/0341999, 2017/0342000, 2017/0342001, and 2016/0375431, and in U.S. Pat. Nos. 10,493,422, 10,464,862, 10,435,336, 10,689,312, and 10,807,921. Generally, the organoaluminum compound can be an aluminoxane, an alkylaluminum compound, or a combination thereof. Representative aluminoxanes include methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-entylaluminoxane, 3-pentyl-aluminoxane, iso-pentyl-aluminoxane, neopentylaluminoxane, and the like, while representative alkylaluminums include trimethylaluminum, triethylaluminum, tripropylaluminum, tributylaluminum, trihexylaluminum, trioctylaluminum, and the like. Often, the Al to Cr molar ratio of the catalyst system can be in a range from 10:1 to 5,000:1, from 50:1 to 3,000:1, from 50:1 to 3,000:1, from 75:1 to 2,000:1, or from 100:1 to 1,000:1.

The oligomerization reactor in which the ethylene oligomer product is formed can comprise any suitable reactor, and non-limiting examples of reactor types can include a stirred tank reactor, a plug flow reactor, or any combination thereof; alternatively, a fixed bed reactor, a continuous stirred tank reactor, a loop reactor, a solution reactor, a tubular reactor, a recycle reactor, or any combination thereof. In an aspect, the oligomerization reactor system can have more than one reactor in series and/or in parallel and can include any combination of reactor types and arrangements. Moreover, the oligomerization process used to form the ethylene oligomer product can be a continuous process or a batch process, or any reactor or reactors within the oligomerization reaction system can be operated continuously or batchwise.

The oligomerization conditions for the various reactor types are well known to those of skill in the art. Nonetheless, a suitable oligomerization temperature typically falls within a range from 0 to 160° C., and more often, the oligomerization temperature is from 40 to 150° C., from 60 to 130° C., from 60 to 115° C., from 70 to 115° C., from 70 to 100° C., or from 75 to 95° C. Suitable pressures will also vary according to the reactor type, but generally, oligomerization pressures fall within a range from 50 psig to 3000 psig. More often, the pressure ranges from 200 psig to 2000 psig, from 400 psig to 1500 psig, from 600 psig to 2000 psig, from 600 psig to 1300 psig, from 700 psig to 1500 psig, or from 700 psig to 1200 psig.

The ethylene oligomer product can contain $C_4$+ hydrocarbons, and generally the vast majority of the ethylene oligomer product is $C_6$ olefins and/or $C_8$ olefins. Thus, the ethylene oligomers include $C_6$ olefins (e.g., 1-hexene), $C_8$ olefins (e.g., 1-octene), and $C_{10}$+ olefins. In an aspect, the major ethylene oligomer in the oligomer product is 1-hexene, while in another aspect, the major ethylene oligomer in the oligomer product is 1-octene, and in yet another aspect, the major ethylene oligomers in the oligomer product are 1-hexene and 1-octene (a mixture thereof).

As a general rule, the total amount of $C_6$ olefins and $C_8$ olefins—based on the total weight of oligomers in the ethylene oligomer product—can be at least 50 wt. %, and more often, at least 65 wt. %, at least 75 wt. %, or at least 85 wt. %, although not limited thereto. After the ethylene oligomer product is discharged in an effluent stream from the oligomerization reactor, the various components can be separated or fractionated into various ethylene oligomer product streams, such as a $C_6$ olefin product stream (e.g., containing predominantly 1-hexene), a $C_8$ olefin product stream (e.g., containing predominantly 1-octene), and so forth.

Referring now to the second process, and similar to the step (c) options in the first process, the step (C) options in the second process are (C1) contacting a polymerization catalyst composition, a feed mixture of the first ethylene feed and a second ethylene feed, and an optional olefin comonomer in a polymerization reactor system under polymerization conditions to produce the ethylene polymer, and/or (C2) contacting an oligomerization catalyst composition with a feed mixture of the first ethylene feed and a second ethylene feed in an oligomerization reactor system under oligomerization conditions to produce the ethylene oligomers. In the second process, ethylene derived or formed in step (A) and step (B) from ethanol is the first ethylene feed, while the second ethylene feed is derived from a plastic, a mixed solid waste stream, or a combination thereof.

The second ethylene feed can be produced via several different methods, including gasification, pyrolysis, hydrothermal liquefaction, and combustion, although not limited thereto. In one aspect, for example, the second ethylene feed can be derived by (or produced by a processes that comprises) (I) gasifying a mixture of an oxygen-containing gasifying agent (e.g., steam and/or oxygen gas) and the plastic, the mixed solid waste stream, or the combination thereof, to form a Syngas stream, (II) separating CO and $H_2$ from the Syngas stream, (III) contacting the CO, $H_2$, and a multicomponent catalyst to form a reaction mixture containing ethylene, and (IV) separating at least a portion (and in some cases, all) of the ethylene from the reaction mixture in step (III) to form the second ethylene feed. The separating can utilize any suitable technique, including extraction, filtration, evaporation, distillation, and the like, as well as combinations thereof.

Additionally or alternatively, the second ethylene feed can be derived by (or produced by a processes that comprises) (I) gasifying a mixture of an oxygen-containing gasifying agent and the plastic, the mixed solid waste stream, or the combination thereof, to form a Syngas stream, and (II) separating at least a portion (and in some cases, all) of ethylene from the Syngas stream in step (I) to form the second ethylene feed. The separating can utilize any suitable technique, including extraction, filtration, evaporation, distillation, and the like, as well as combinations thereof.

Additionally or alternatively, the second ethylene feed can be derived by (or produced by a processes that comprises) (I) subjecting the plastic, the mixed solid waste stream, or the combination thereof, to pyrolysis to form a pyrolysis oil, (II) cracking the pyrolysis oil to form a mixed hydrocarbon stream containing ethylene, and (III) separating at least a portion (and in some cases, all) of the ethylene from the mixed hydrocarbon stream in step (II) to form the second ethylene feed. The separating can utilize any suitable technique, including extraction, filtration, evaporation, distillation, and the like, as well as combinations thereof. A particular type of pyrolysis, often referred to as fast pyrolysis, can be utilized herein, in part due to its advantageous scalability, low capital cost, and high liquid production yields, as well as the use of moderate temperatures (e.g., 400-650° C.) in the absence of oxygen in, for example, a fluidized bed reactor to produce the pyrolysis oil.

Referring now to both the first process and the second process for producing an ethylene polymer and/or ethylene oligomers, at least a portion (and in some cases, all) of the water removed from the reaction mixture in step (b) and step (B) can be subjected to electrolysis to form $O_2$ and $H_2$. Any suitable source of electricity can be utilized to power the electrolysis process, but in some aspects, a green source of electricity, such as wind energy, solar energy, and the like, can be used to conduct the electrolysis of water to form $O_2$ and $H_2$. Advantageously, at least a portion (and in some cases, all) of the $O_2$ produced via electrolysis can be used as the gasifying agent to form the Syngas stream.

Optionally, the first process and the second process can further comprise a step of processing air through an air separation unit to form $N_2$ and $O_2$. Beneficially, at least a portion (and in some cases, all) of the $O_2$ from the air separation unit can be used as the gasifying agent to form the Syngas stream.

Another step that be integrated with the first process and the second process is a step of contacting $H_2$, $N_2$, and an ammonia synthesis catalyst to form ammonia. Using product streams from the air separation unit and from electrolysis, at least a portion (and in some cases, all) of the $N_2$ from the air separation unit and/or the at least a portion (and in some cases, all) of the $H_2$ from the electrolysis stream is/are used as the reactants to form the ammonia. Additionally or alternatively, a portion of the $H_2$ from the Syngas stream can be used in addition to, or in place of, the $H_2$ from the electrolysis stream.

A further step that be integrated with the first process and the second process is a step of contacting $CO_2$ and at least a portion (and in some cases, all) of the ammonia (which was produced from $H_2$ and $N_2$) to form urea. In some aspects, at least a portion (and in some cases, all) of the $CO_2$ from the Syngas stream is used in conjunction with ammonia to form the urea. The urea, thus formed, can be used as a fertilizer, thus promoting the production of biomass products that can be used to form ethanol, for example, via fermentation.

Referring now to FIG. 1, which illustrates a schematic flow diagram of a process 100 for converting ethanol into an ethylene polymer and/or ethylene oligomers consistent with an aspect of the present disclosure. A waste source 105 and a gasifying agent 103 are gasified 110 to form a Syngas stream 115. The waste source 105 can be any disclosed herein, such as biomass, plastic, mixed solid waste, and the like, and this include mixtures or combinations of these sources. The Syngas stream 115 is separated or purified 120, resulting in a CO and $H_2$ stream 125. The CO and $H_2$ stream 125 is catalytically converted 130 to Syngas-derived ethanol 137. The Syngas-derived ethanol 137 can be mixed with bioethanol 133 (ethanol derived from biomass) in any relative proportions to form a combined ethanol stream 135, which is catalytically converted 140 to a reaction mixture 145 that contains ethylene.

The reaction mixture 145 in FIG. 1 is subjected to a suitable heat source 148 and separated 150 into a purified ethylene stream 155 and a water by-product stream 152. The ethylene stream 155 is polymerized/oligomerized 160 to form an ethylene polymer and/or ethylene oligomers 165. Some of this product stream 162 can be recycled, for instance, gasified 110 to form the Syngas stream, if desired. Another portion of the ethylene polymer and/or ethylene oligomers 165 is used as a desired end-use product 168, such as an article of manufacture produced from the ethylene polymers. After use, it is also possible to recycle the article of manufacture (e.g., post-consumer recycle) by gasifying 110 to produce Syngas.

Electrolysis and air separation are collectively in 170. Water 172 can be subjected to electrolysis 170, using some or all of the by-product water stream 152 to form $O_2$ and $H_2$. Air 174 can be processed through air separation unit 170 to produce $N_2$ and $O_2$. If desired, $O_2$ from electrolysis and air separation 170 can be used as gasifying agent 103. The resulting $N_2$ and $H_2$ streams 175 from electrolysis and air separation 170 can be catalytically converted 180 to form ammonia 185.

Figure 2:
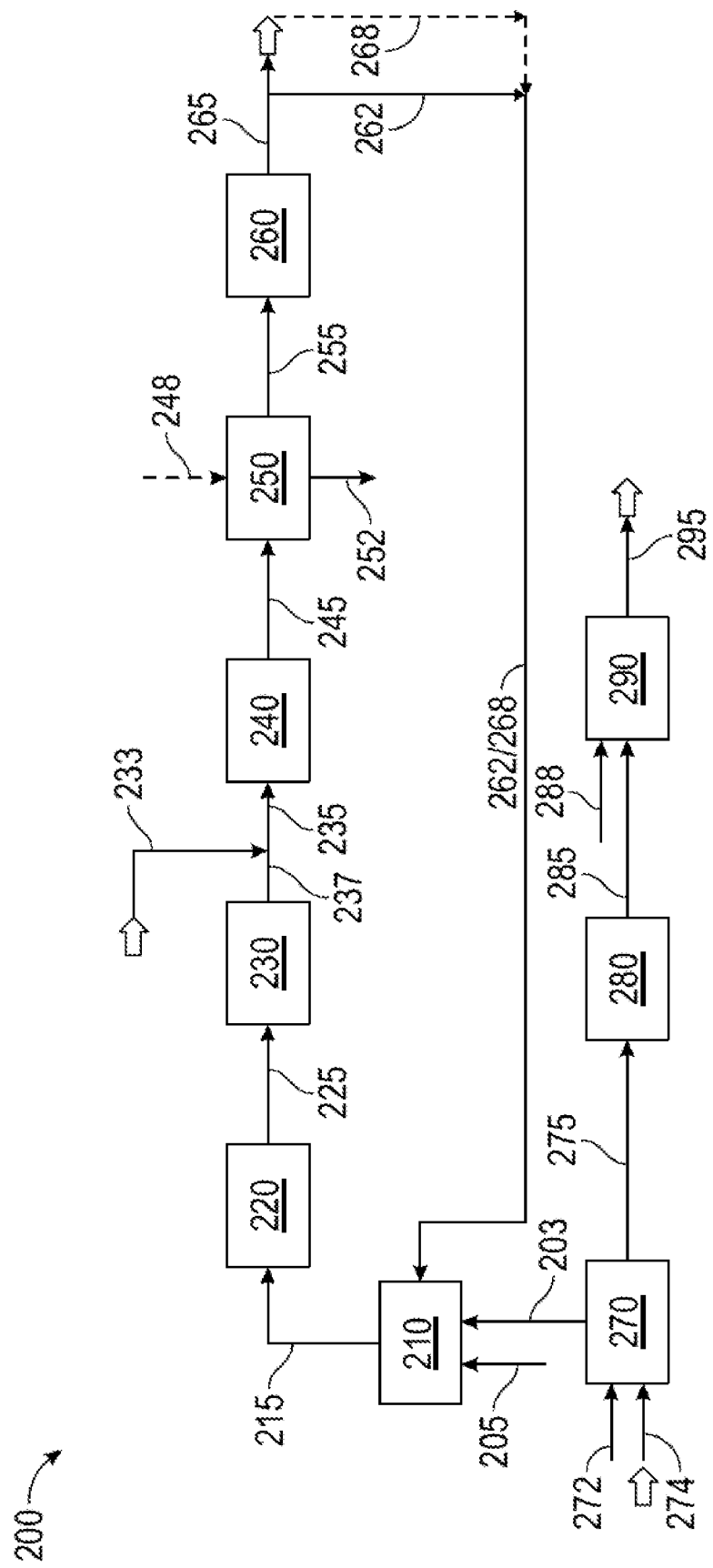
FIG. 2 is a schematic flow diagram of a process for converting ethanol into an ethylene polymer and/or ethylene oligomers consistent with another aspect of the present disclosure.

Referring now to FIG. 2, which illustrates an alternative process 200 for converting ethanol into an ethylene polymer and/or ethylene oligomers consistent with another aspect of the present disclosure. The reference numerals in FIG. 2 are generally the same as described for the similarly numbered components in FIG. 1, with the following exceptions. In FIG. 2, the resulting $N_2$ and $H_2$ streams 275 from electrolysis and air separation 270 are catalytically converted 280 to form ammonia 285, which is combined with $CO_2$ 288 and converted 290 into a urea product stream 295.

Figure 3A:
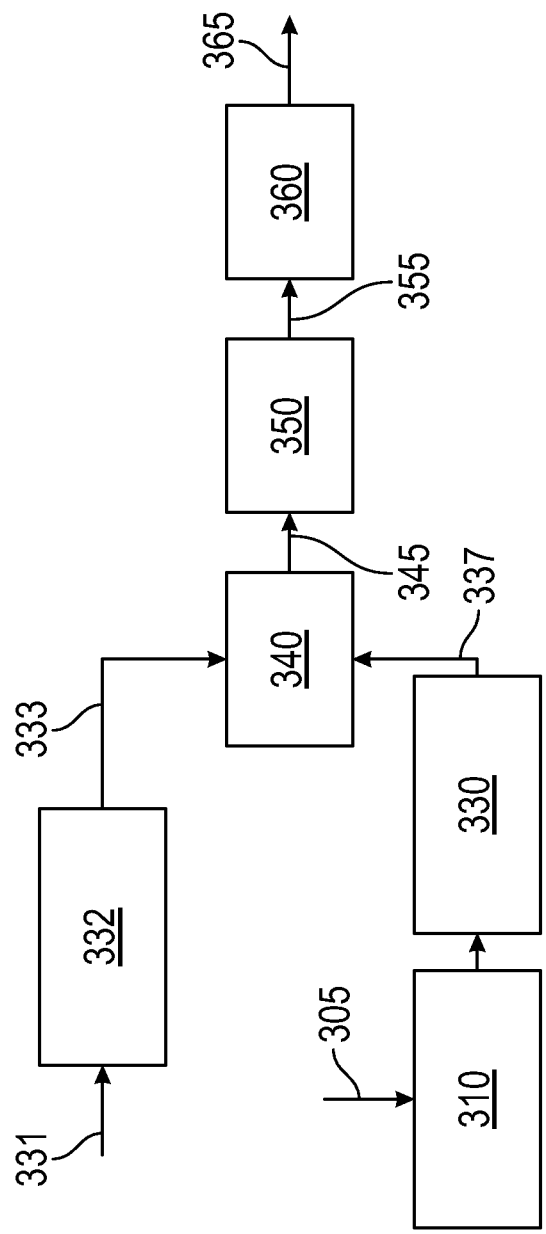
FIGS. 3A-3F illustrate different options for deriving ethanol and/or ethylene that can be integrated into the processes of FIGS. 1-2.

In FIGS. 3A-3F, different options for deriving ethanol and/or ethylene are illustrated, and these can be integrated into the processes shown and described in FIGS. 1-2, as well as the first and second processes disclosed herein. Referring first to FIG. 3A, this process shows the catalytic conversion 340 of ethanol to form reaction mixture 345 that contains ethylene and undergoes a separation step 350, thereby forming a purified ethylene stream 355, which is polymerized/oligomerized 360 to form an ethylene polymer and/or ethylene oligomers 365, and these are generally the same as described for the similarly numbered components in FIG. 1. In FIG. 3A, a biomass source 331 is fermented 332 to form bioethanol 333 (ethanol derived from biomass), which is one source of ethanol. The other source of ethanol is Syngas-derived ethanol 337, in which a waste source 305 (e.g., plastic, mixed solid waste) is gasified 310 to form a Syngas stream, which is purified as needed, and then catalytically converted 330 to form Syngas-derived ethanol 337.

Figure 3B:
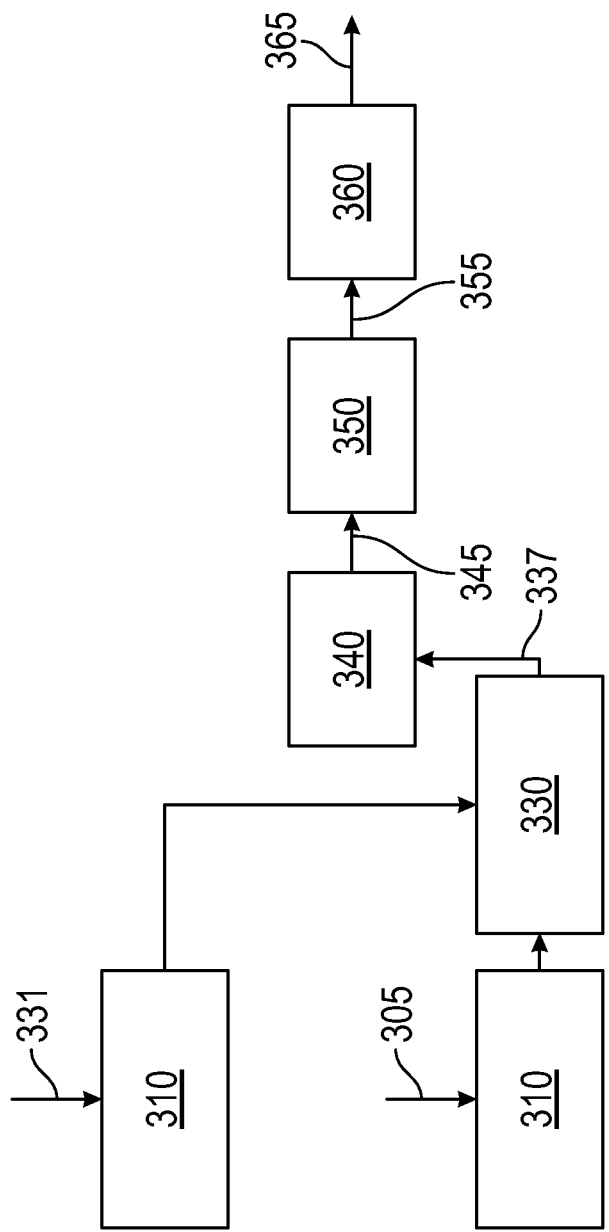

The multistep conversion of ethanol to form an ethylene polymer and/or ethylene oligomers (340, 345, 350, 355, 360, 365) in FIG. 3B is same as shown in FIG. 3A. However, in FIG. 3B, a biomass source 331 is gasified 310 to form a Syngas stream, and a waste source 305 (e.g., plastic, mixed solid waste) is gasified 310 to form a Syngas stream. These two Syngas streams can be purified as needed and subsequently catalytically converted 330 to form Syngas-derived ethanol 337 from two sources.

Figure 3C:
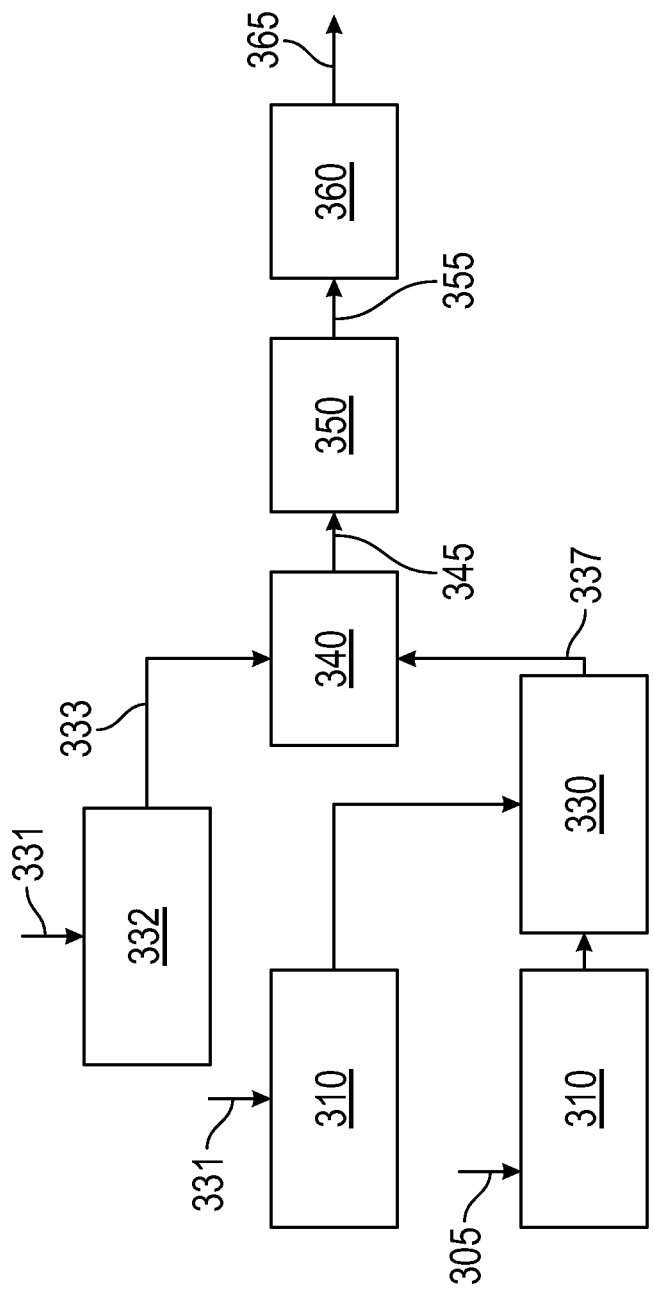

Similarly, the multistep conversion of ethanol to form an ethylene polymer and/or ethylene oligomers (340, 345, 350, 355, 360, 365) in FIG. 3C is same as shown in FIG. 3A. However, in FIG. 3C, a biomass source 331 is fermented 332 to form bioethanol 333 (ethanol derived from biomass), which is one source of ethanol. Additionally, a biomass source 331 (the same as or different from the biomass sources for fermenting 332) is gasified 310 to form a Syngas stream, and a waste source 305 (e.g., plastic, mixed solid waste) is gasified 310 to form a Syngas stream. These two Syngas streams can be purified as needed, and then catalytically converted 330 to form Syngas-derived ethanol 337 from two sources.

Figure 3D:
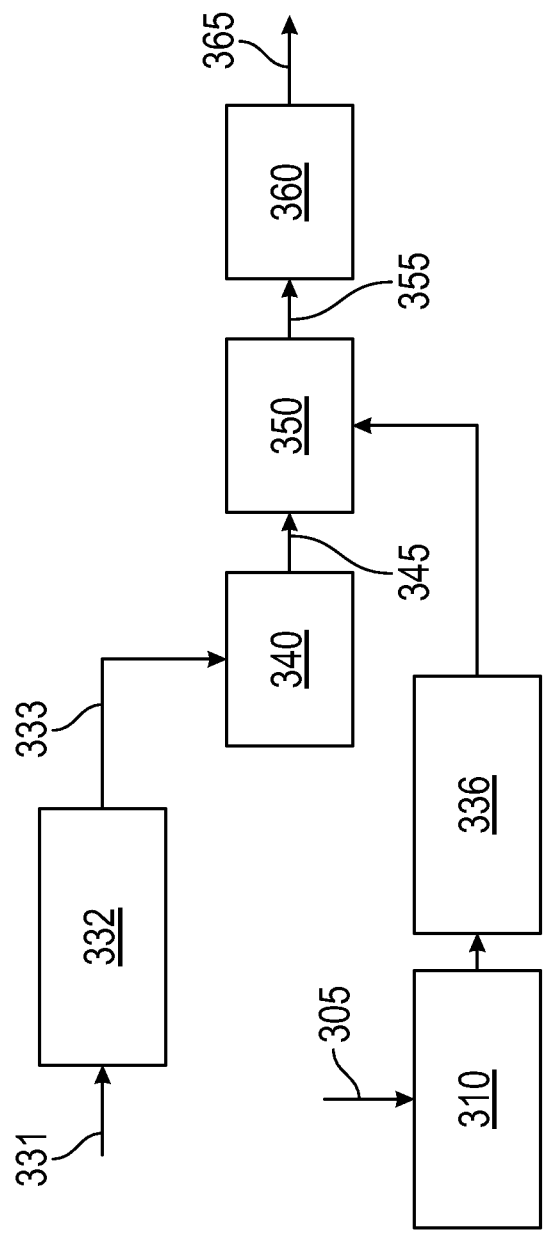

The multistep conversion of ethanol to form an ethylene polymer and/or ethylene oligomers (340, 345, 350, 355, 360, 365) in FIG. 3D is same as shown in FIG. 3A. However, a waste source 305 (e.g., plastic, mixed solid waste) in FIG. 3D is gasified 310 to form a Syngas stream, which is purified as needed and then catalytically converted 336 directly to an ethylene-containing stream. Using an appropriate catalyst and reaction conditions, ethylene can be selectively produced instead of ethanol. Thus, the process of FIG. 3D uses two sources of ethylene, one from ethanol via biomass 331 and the other from Syngas via the waste source 305.

Figure 3E:
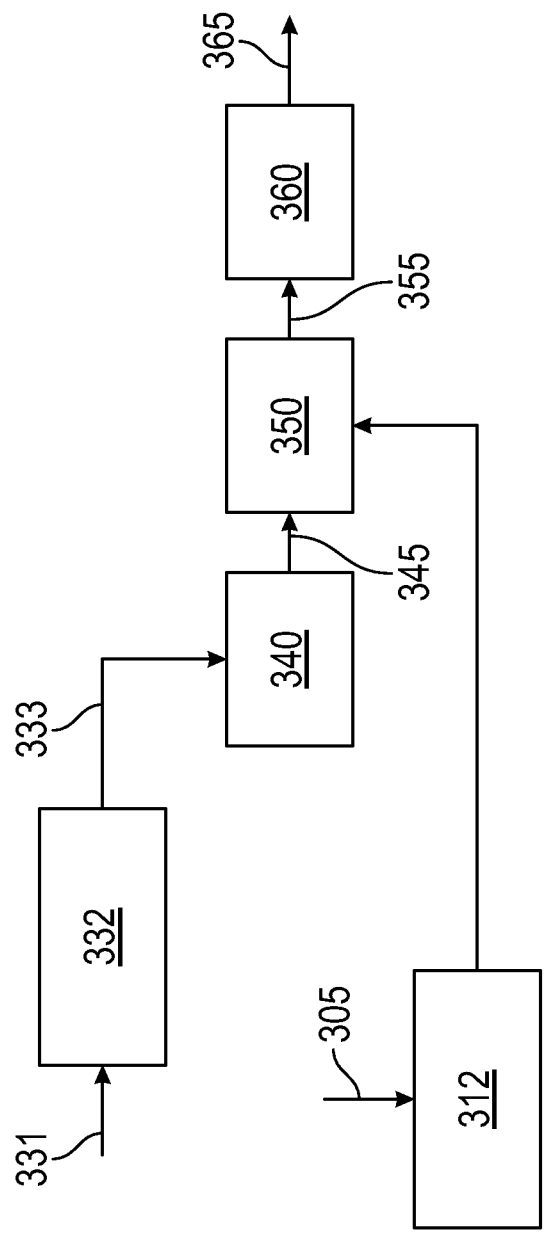

FIG. 3E is a variation of FIG. 3D in which the waste source 305 (e.g., plastic, mixed solid waste) is subjected to pyrolysis to form a pyrolysis oil, which is then cracked to form a mixed hydrocarbon stream containing ethylene. This conversion is referred to collectively as 312 in FIG. 3E. The mixed hydrocarbon stream from this conversion contains ethylene and undergoes a purification step 350 (the same as or a different purification step 350 for the reaction mixture 345) to form purified ethylene stream 355. Thus, the process of FIG. 3E uses two sources of ethylene, one from ethanol via biomass 331 and the other from pyrolysis/cracking of the waste source 305.

Figure 3F:
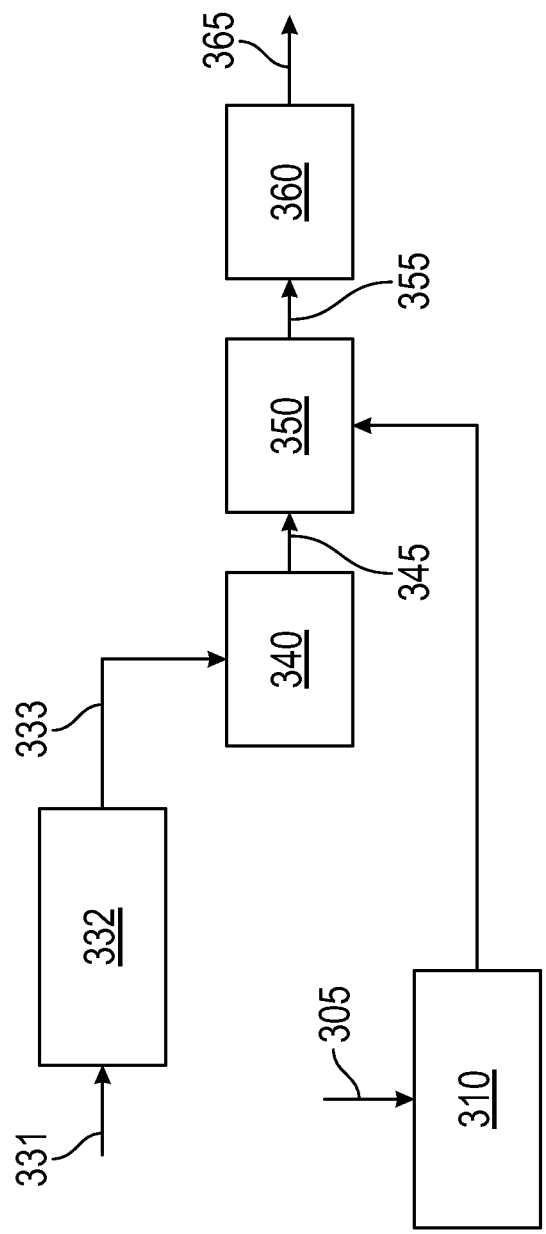

FIG. 3F is a variation of FIG. 3D in which the waste source 305 (e.g., plastic, mixed solid waste) is gasified 310 to form a Syngas stream containing ethylene. This Syngas containing ethylene undergoes a purification step 350 (the same as or a different purification step 350 for the reaction mixture 345) to form a purified ethylene stream 355. Thus, the process of FIG. 3F uses two sources of ethylene, one from ethanol via biomass 331 and the other from Syngas via the waste source 305.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for converting ethanol into an ethylene polymer and/or ethylene oligomers, the process comprising (a) contacting the ethanol and a catalyst to produce a reaction mixture containing ethylene, wherein a first portion of the ethanol is derived from a biomass and a second portion of the ethanol is derived from a plastic, a mixed solid waste stream, or a combination thereof; (b) separating at least a portion (and in some cases, all) of the ethylene from the reaction mixture; and (c1) contacting a polymerization catalyst composition with the ethylene and an optional olefin comonomer in a polymerization reactor system under polymerization conditions to produce the ethylene polymer, and/or (c2) contacting an oligomerization catalyst composition with the ethylene in an oligomerization reactor system under oligomerization conditions to produce the ethylene oligomers.

Aspect 2. A process for producing an ethylene polymer and/or ethylene oligomers, the process comprising (A) contacting ethanol and a catalyst to produce a reaction mixture containing ethylene, wherein a first portion of the ethanol is derived from a biomass and an optional second portion of the ethanol is derived from a plastic, a mixed solid waste stream, or a combination thereof; (B) separating at least a portion (and in some cases, all) of the ethylene from the reaction mixture to form a first ethylene feed; and (C1) contacting a polymerization catalyst composition, a feed mixture of the first ethylene feed and a second ethylene feed, and an optional olefin comonomer in a polymerization reactor system under polymerization conditions to produce the ethylene polymer, and/or (C2) contacting an oligomerization catalyst composition with a feed mixture of the first ethylene feed and a second ethylene feed in an oligomerization reactor system under oligomerization conditions to produce the ethylene oligomers; wherein the second ethylene feed is derived from a plastic, a mixed solid waste stream, or a combination thereof.

Aspect 3. The process defined in aspect 2, wherein a weight ratio of the first ethylene feed to the second ethylene feed in the feed mixture is in any suitable range, e.g., from 50:1 to 1:50, from 10:1 to 1:10, from 5:1 to 1:5, or from 2:1 to 1:2.

Aspect 4. The process defined in any one of aspects 1-3, wherein a weight ratio of the first portion of the ethanol to the second portion of the ethanol is in any suitable range, e.g., from 50:1 to 1:50, from 10:1 to 1:10, from 5:1 to 1:5, or from 2:1 to 1:2.

Aspect 5. The process defined in any one of aspects 1-4, wherein the second portion of the ethanol is derived by (i) gasifying a mixture of an oxygen-containing gasifying agent and the plastic, the mixed solid waste stream, or the combination thereof, to form a Syngas stream; (ii) separating CO and $H_2$ from the Syngas stream; and (iii) contacting the CO, $H_2$, and a multicomponent catalyst to form a reaction mixture containing ethanol.

Aspect 6. The process defined in any one of aspects, 1-5, wherein the first portion of the ethanol is derived by fermenting the biomass to produce ethanol and a biomass by-product.

Aspect 7. The process defined in aspect 6, wherein the process further comprises a step of separating at least a portion (and in some cases, all) of the ethanol from the biomass by-product using any suitable technique or any technique disclosed herein, e.g., extraction, filtration, evaporation, distillation, or any combination thereof.

Aspect 8. The process defined in any one of aspects, 1-7, wherein the first portion of the ethanol is derived by (i) gasifying a mixture of an oxygen-containing gasifying agent and the biomass (and/or the biomass by-product) to form a Syngas stream; (ii) separating CO and $H_2$ from the Syngas stream; and (iii) contacting the CO, $H_2$, and a multicomponent catalyst to form a reaction mixture containing ethanol.

Aspect 9. The process defined in any one of aspects 5-8, wherein the process further comprises a step of separating at least a portion (and in some cases, all) of the ethanol from the reaction mixture in step (iii) and prior to step (a) and step (A), using any suitable technique or any technique disclosed herein, e.g., extraction, filtration, evaporation, distillation, or any combination thereof.

Aspect 10. The process defined in any one of aspects 5-9, wherein the gasifying agent is not air.

Aspect 11. The process defined in any one of aspects 5-10, wherein the gasifying agent comprises $H_2O$ (steam), $O_2$, and/or $CO_2$.

Aspect 12. The process defined in any one of aspects 5-11, wherein the gasifying agent contains less than 1 mol % nitrogen.

Aspect 13. The process defined in any one of aspects 1-12, wherein the reaction mixture in step (a) and step (A) further comprises water, and step (b) and step (B) further comprise separating water from the reaction mixture.

Aspect 14. The process defined in any one of aspects 1-13, wherein separating in step (b) and step (B) comprises any suitable technique or any technique disclosed herein, e.g., extraction, filtration, evaporation, distillation, or any combination thereof.

Aspect 15. The process defined in aspect 13 or 14, wherein the process further comprises a step of subjecting at least a portion (and in some cases, all) of the water from step (b) and step (B) to electrolysis to form $O_2$ and $H_2$.

Aspect 16. The process defined in aspect 15, wherein at least a portion (and in some cases, all) of the $O_2$ is used as the gasifying agent to form the Syngas stream.

Aspect 17. The process defined in aspect 15 or 16, wherein the electrolysis utilizes a green source of electricity (e.g., wind energy, solar energy).

Aspect 18. The process defined in any one of aspects 1-17, wherein the process further comprises a step of processing air through an air separation unit to form $N_2$ and $O_2$.

Aspect 19. The process defined in aspect 18, wherein at least a portion (and in some cases, all) of the $O_2$ is used as the gasifying agent to form the Syngas stream.

Aspect 20. The process defined in any one of aspects 1-19, wherein the process further comprises a step of contacting $H_2$, $N_2$, and an ammonia synthesis catalyst to form ammonia.

Aspect 21. The process defined in aspect 20, wherein at least a portion (and in some cases, all) of the $N_2$ from the air separation unit and/or the $H_2$ from the electrolysis stream is/are used to form the ammonia.

Aspect 22. The process defined in aspect 20 or 21, wherein the process further comprises a step of contacting $CO_2$ and at least a portion (and in some cases, all) of the ammonia to form urea.

Aspect 23. The process defined in aspect 22, wherein at least a portion (and in some cases, all) of the $CO_2$ from the Syngas stream is used to form the urea.

Aspect 24. The process defined in any one of aspects 1-23, wherein the polymerization catalyst composition is a met-allocene catalyst system, a Ziegler-Natta catalyst system, a chromium catalyst system, or any combination thereof.

Aspect 25. The process defined in any one of aspects 1-24, wherein the ethylene polymer comprises an ethylene homopolymer and/or an ethylene/α-olefin copolymer.

Aspect 26. The process defined in any one of aspects 1-25, wherein the ethylene polymer comprises an ethylene homopolymer, an ethylene/1-butene copolymer, an ethylene/1-hexene copolymer, and/or an ethylene/1-octene copolymer.

Aspect 27. The process defined in any one of aspects 1-26, wherein the oligomerization catalyst composition is a chromium catalyst system.

Aspect 28. The process defined in any one of aspects 1-27, wherein the oligomerization catalyst composition comprises a heteroatomic ligand chromium compound complex and an organoaluminum compound, or a heteroatomic ligand, a chromium compound, and an organoaluminum compound.

Aspect 29. The process defined in any one of aspects 1-28, wherein the ethylene oligomers comprise $C_6$ olefins (e.g., 1-hexene), $C_8$ olefins (e.g., 1-octene), and $C_{10}$+ olefins.

Aspect 30. The process defined in any one of aspects 2-29, wherein the second ethylene feed is derived by (I) gasifying a mixture of an oxygen-containing gasifying agent and the plastic, the mixed solid waste stream, or the combination thereof, to form a Syngas stream; (II) separating CO and $H_2$ from the Syngas stream; (III) contacting the CO, $H_2$, and a multicomponent catalyst to form a reaction mixture containing ethylene; and (IV) separating at least a portion (and in some cases, all) of the ethylene from the reaction mixture in step (III) to form the second ethylene feed, using any suitable technique or any technique disclosed herein, e.g., extraction, filtration, evaporation, distillation, or any combination thereof.

Aspect 31. The process defined in any one of aspects 2-30, wherein the second ethylene feed is derived by (I) gasifying a mixture of an oxygen-containing gasifying agent and the plastic, the mixed solid waste stream, or the combination thereof, to form a Syngas stream; and (II) separating at least a portion (and in some cases, all) of ethylene from the Syngas stream in step (I) to form the second ethylene feed, using any suitable technique or any technique disclosed herein, e.g., extraction, filtration, evaporation, distillation, or any combination thereof.

Aspect 32. The process defined in any one of aspects 2-31, wherein the second ethylene feed is derived by (I) subjecting the plastic, the mixed solid waste stream, or the combination thereof, to pyrolysis to form a pyrolysis oil; (II) cracking the pyrolysis oil to form a mixed hydrocarbon stream containing ethylene; and (III) separating at least a portion (and in some cases, all) of the ethylene from the mixed hydrocarbon stream in step (II) to form the second ethylene feed, using any suitable technique or any technique disclosed herein, e.g., extraction, filtration, evaporation, distillation, or any combination thereof.

We claim:

1. A process for converting ethanol into an ethylene polymer and/or ethylene oligomers, the process comprising:
    (a1) fermenting a biomass source to produce a first portion of ethanol and a biomass by-product; or
    (a2) anaerobically digesting a biomass source to produce a first portion of ethanol and a biomass by-product; or
    (a3) gasifying a mixture of a first oxygen-containing gasifying agent and a biomass source to form a first Syngas stream, separating CO and $H_2$ from the first Syngas stream, and contacting the CO, $H_2$, and a first multicomponent catalyst to form a first reaction mixture containing a first portion of ethanol;
(b) gasifying a mixture of a second oxygen-containing gasifying agent and a plastic, a mixed solid waste stream, or a combination thereof, to form a second Syngas stream, separating CO and $H_2$ from the second Syngas stream, and contacting the CO, $H_2$, and a second multicomponent catalyst to form a second reaction mixture containing a second portion of ethanol;
(c) contacting the first portion of the ethanol, the second portion of the ethanol, and a catalyst to produce a third reaction mixture containing ethylene;
(d) separating at least a portion of the ethylene from the third reaction mixture; and
(e1) contacting a polymerization catalyst composition with the ethylene and an optional olefin comonomer in a polymerization reactor system under polymerization conditions to produce the ethylene polymer, and/or
(e2) contacting an oligomerization catalyst composition with the ethylene in an oligomerization reactor system under oligomerization conditions to produce the ethylene oligomers.

2. The process of claim 1, wherein a weight ratio of the first portion of the ethanol to the second portion of the ethanol is in a range from 50:1 to 1:50.

3. The process of claim 1, wherein the process comprises step (a1).

4. The process of claim 3, wherein the process further comprises a step of separating the first portion of the ethanol from the biomass by-product.

5. The process of claim 1, wherein the process comprises step (a2).

6. The process of claim 1, wherein the process comprises step (a3).

7. The process of claim 6, wherein the process further comprises a step of separating the first portion of the ethanol from the first reaction mixture.

8. The process of claim 1, wherein the first oxygen-containing gasifying agent and the second oxygen-containing gasifying agent independently comprise $H_2O$/steam, $O_2$, and/or $CO_2$.

9. The process of claim 1, wherein:
the third reaction mixture in step (c) further comprises water, and step (d) further comprises separating water from the third reaction mixture; and
the process further comprises a step of subjecting at least a portion of the water from step (d) to electrolysis to form $O_2$ and $H_2$, and at least a portion of the $O_2$ is used as the first gasifying agent and/or the second gasifying agent.

10. The process of claim 1, wherein the process further comprises a step of processing air through an air separation unit to form $N_2$ and $O_2$, and at least a portion of the $O_2$ is used as the first oxygen-containing gasifying agent and/or the second oxygen-containing gasifying agent.

11. The process of claim 1, wherein:
the process further comprises a step of contacting $H_2$, $N_2$, and an ammonia synthesis catalyst to form ammonia; and
at least a portion of $N_2$ from an air separation unit and/or $H_2$ from an electrolysis stream is/are used to form the ammonia.

12. The process of claim 11, wherein:
the process further comprises a step of contacting $CO_2$ and at least a portion of the ammonia to form urea; and at least a portion of $CO_2$ from the first Syngas stream and/or the second Syngas stream is used to form the urea.

13. The process of claim 1, wherein:
the process comprises step (e1);
the polymerization catalyst composition is a metallocene catalyst system, a Ziegler-Natta catalyst system, a chromium catalyst system, or any combination thereof, and
the ethylene polymer comprises an ethylene homopolymer, an ethylene/1-butene copolymer, an ethylene/1-hexene copolymer, and/or an ethylene/1-octene copolymer.

14. The process of claim 1, wherein:
the process comprises step (e2);
the oligomerization catalyst composition is a chromium catalyst system; and
the ethylene oligomers comprise 1-hexene, 1-octene, and $C_{10+}$ olefins.

15. A process for producing an ethylene polymer and/or ethylene oligomers, the process comprising:
(A) contacting ethanol and a catalyst to produce a first reaction mixture containing ethylene, and separating at least a portion of the ethylene from the first reaction mixture to form a first ethylene feed;
(B1) gasifying a mixture of a first oxygen-containing gasifying agent and a plastic, a mixed solid waste stream, or a combination thereof, to form a first Syngas stream, separating CO and $H_2$ from the first Syngas stream, contacting the CO, $H_2$, and a multicomponent catalyst to form a second reaction mixture containing ethylene, and separating at least a portion of the ethylene from the second reaction mixture to form a second ethylene feed; or
(B2) gasifying a mixture of a second oxygen-containing gasifying agent and a plastic, a mixed solid waste stream, or a combination thereof, to form a second Syngas stream, and separating at least a portion of ethylene from the second Syngas stream to form a second ethylene feed; or
(B3) subjecting a plastic, a mixed solid waste stream, or a combination thereof, to pyrolysis to form a pyrolysis oil, cracking the pyrolysis oil to form a mixed hydrocarbon stream containing ethylene, and separating at least a portion of the ethylene from the mixed hydrocarbon stream to form a second ethylene feed; and
(C1) contacting a polymerization catalyst composition, a feed mixture of the first ethylene feed and the second ethylene feed, and an optional olefin comonomer in a polymerization reactor system under polymerization conditions to produce the ethylene polymer, and/or
(C2) contacting an oligomerization catalyst composition with a feed mixture of the first ethylene feed and the second ethylene feed in an oligomerization reactor system under oligomerization conditions to produce the ethylene oligomers.

16. The process of claim 15, wherein a weight ratio of the first ethylene feed to the second ethylene feed in the feed mixture is in a range from 50:1 to 1:50.

17. The process of claim 15, wherein the process comprises step (B1).

18. The process of claim 15, wherein the process comprises step (B2).

19. The process of claim 15, wherein the process comprises step (B3).

20. The process of claim 15, wherein a weight ratio of the first ethylene feed to the second ethylene feed in the feed mixture is in a range from 10:1 to 1:10.

* * * * *